(12) United States Patent
Della Ciana et al.

(10) Patent No.: US 9,040,252 B2
(45) Date of Patent: May 26, 2015

(54) METHOD FOR INCREASING AND REGULATING LIGHT EMISSION FROM A CHEMILUMINESCENT REACTION

(75) Inventors: Leopoldo Della Ciana, Bologna (IT); Federica Rodeghiero, Bologna (IT); Rossana Perciaccante, Bologna (IT)

(73) Assignee: Cyanagen S.R.L., Bologna (IT)

( * ) Notice: Subject to any disclaimer, the term of this patent is extended or adjusted under 35 U.S.C. 154(b) by 327 days.

(21) Appl. No.: 13/167,137

(22) Filed: Jun. 23, 2011

(65) Prior Publication Data
US 2012/0009603 A1    Jan. 12, 2012

(30) Foreign Application Priority Data

Jul. 6, 2010    (IT) .............................. TO2010A0580

(51) Int. Cl.
| | | |
|---|---|---|
| *G01N 21/76* | (2006.01) | |
| *G01N 33/53* | (2006.01) | |
| *G01N 33/58* | (2006.01) | |
| *C12Q 1/28* | (2006.01) | |

(52) U.S. Cl.
CPC ................ *G01N 33/582* (2013.01); *C12Q 1/28* (2013.01); *G01N 33/5306* (2013.01)

(58) Field of Classification Search
None
See application file for complete search history.

(56) References Cited

U.S. PATENT DOCUMENTS

| 4,950,588 A | 8/1990 | Dattagupta |
|---|---|---|
| 2003/0073150 A1 | 4/2003 | Woerner et al. |
| 2008/0241868 A1 * | 10/2008 | Della Ciana ................... 435/28 |

FOREIGN PATENT DOCUMENTS

EP    1962095    8/2008

OTHER PUBLICATIONS

European Search Report issued Aug. 26, 2011 in connection with EP Application No. 11172336.7.
Italian Search Report for IT TO2010A000580 dated Feb. 1, 2011.
Non-English Written Opinion dated Jul. 6, 2010, IT TO2010A000580.

* cited by examiner

*Primary Examiner* — Galina Yakovleva
(74) *Attorney, Agent, or Firm* — Nixon & Vanderhye PC

(57) ABSTRACT

Method for increasing and regulating the emission of light from a chemiluminescent reaction including luminol, a peroxidase enzyme, an oxidant and an electron mediator (primary enhancer) through the use of an acylation catalyst (secondary enhancer) belonging to the class of N-azoles, i.e., a class of five-membered nitrogen heteroaromatic ring compounds containing at least one other atom of nitrogen. N-azoles, which are especially useful as secondary enhancers are imidazole, 1-methylimidazole, 1,2,3-triazole and 1,2,4-triazole. The invention also describes the use in diagnostic assays of chemiluminescent substrates containing said N-azoles, as secondary enhancers.

14 Claims, 4 Drawing Sheets

METHOD FOR INCREASING AND REGULATING LIGHT EMISSION FROM A CHEMILUMINESCENT REACTION

This application claims priority to IT Patent Application No. TO2010A000580 filed 6 Jul. 2010, the entire contents of which is hereby incorporated by reference.

FIELD OF THE INVENTION

The present invention concerns a new method for increasing and regulating light emission generated by the chemiluminescent reaction of luminol, a peroxidase enzyme, an oxidant and an electron mediator.

BACKGROUND ART

The chemiluminescent oxidation of luminol catalyzed by peroxidase finds wide employment in analytical test of antigens, antibodies and nucleic acids, and in particular blotting tests, e.g. Dot Blots, Western Blots (proteins), Southern and Northern Blots (nucleic acids).

It is known that the chemiluminescent oxidation of luminol catalyzed by peroxidase can be made faster and more efficient by adding an electron mediator, or enhancer, as shown, for example, by L. J. Kricka in Clinical Chemistry 1991; 37:1472-1481; or by L. J. Kricka, J. C: Voyta and I. Bronstein in "Chemiluminescent Methods for Detecting and Quantitating Enzyme Activity", Methods Enzymol. 2000; 305:370-390. Several compounds have been used as electron mediators, including luciferin, 6-hydroxybenzotriazols, p-iodophenols, p-coumaric acid are described by G. H. G. Thorpe and L. J. Kricka, Methods Enzymol. 1986; 133:331; aromatic amines in U.S. Pat. No. 4,279,950; acetanilides in Eur. Pat. Appl. No. 603953 (1994); N-substituted phenothiazines in U.S. Pat. No. 5,171,688; boronic acids in U.S. Pat. No. 5,629,168. It is believed that, in the presence of an electron mediator, the oxidation of luminal catalyzed by peroxidase proceeds according to the following scheme:

$$HRP + H_2O_2 \rightarrow HRP\text{-}I \tag{1}$$

$$HRP\text{-}I + LH^- \rightarrow HRP\text{-}II + L.^- \tag{2}$$

$$HRP\text{-}II + LH^- \xrightarrow{HRP + L.^-} \tag{3}$$

$$HRP\text{-}I + E \rightarrow HRP\text{-}II + E.^- \tag{4}$$

$$HRP\text{-}II + E \rightarrow HRP + E.^- \tag{5}$$

$$E.^- + LH^- \rightarrow E + L.^- \tag{6}$$

$$L.^- \rightarrow L + LH^- \tag{7}$$

$$L + H_2O_2 \rightarrow LO_2^{2-} \tag{8}$$

$$LO_2^{2-} \rightarrow AP^{2-*} \tag{9}$$

$$AP^{2-*} \rightarrow AP^{2-} + h\nu \tag{10}$$

where HRP, HRP-I and HRP-II indicate the enzyme peroxidase in the native and its two oxidized forms, respectively; LH—, L.$^-$, L and LO$_2^{2-}$ represent luminol anion, luminol radical anion, diazaquinone and luminol peroxide; E and E.$^-$ represent the electron mediator, or primary enhancer, and its corresponding radical; finally AP$^{2-}$ indicates the dianion of 3-aminophthalic acid and AP$^{2-}$* its excited state. According to this scheme, peroxidase HRP is oxidized by peroxide to HRP-I. The luminol anion and the primary enhancer are oxidized by HRP-I to their respective radicals with conversion of the enzyme to its HRP-II form. In turn, HRP-II oxidizes another molecule of luminol anion or of primary enhancer to their respective radicals, simultaneously regenerating the native form of the HRP enzyme, which can participate in another oxidation cycle.

The increase in light output observed in the presence of an electron mediator E is attributed to the faster generation of the key intermediate L.$^-$ (see, e.g. S. B: Vlasenko, A. A. Arefeyev, A. D. Klimov, B. B. Kim, E. L. Gorovits, A. P. Osipov, E. M. Gavrilova, A. M. Yegorov, J. Biolumin. Chemilumin. 1989; 4: 164-176). Once formed, L.$^-$ quickly dismutates to luminol anion LH$^-$ and diazaquinone, L. The diazaquinone is susceptible to nucleophilic attack on the carbonilic carbon (C=O) by peroxide, with formation of luminol peroxide. Finally, the luminol peroxide collapses to 3-aminophthalate in its excited form, AP$^{2-}$* with simultaneous expulsion of molecular nitrogen. The excited state of 3-aminophthalate then emits a blue photon at 425 nm.

A further, significant increase in chemiluminescent light emission was obtained through the use of certain acylation catalysts, as described in US Pat. Appl. 2008/0241686 and in E. Marzocchi, S. Grilli, L. Della Ciana, L. Prodi, M. Mirasoli, A. Roda, Anal. Biochem. 2008; 277:189-194. These compounds, belonging to the class of 4-aminopyridines, provide a further enhancement in light output only when used in conjunction with primary, electron transfer type, enhancers. Thus, they can been described as "secondary enhancers", see, e.g., the following references: M. M. Vdovenko, L. Della Ciana, I. Yu. Sakharov, Anal. Biochem. 2009; 392:54-58.

While the 4-aminopyridine catalysts of US Pat. Appl. 2008/0241686 have a powerful effect on the efficiency of the luminol chemiluminescent reaction, they are difficult to regulate. Even very small amounts of the compounds produce a large increase in signal. In addition, the signal decays much faster than in their absence. There are however advantages in providing formulations capable of producing an increased light output combined with a relatively low rate of signal decay. These features are especially valuable when repeated readings are necessary.

For this reasons, it is a valuable advance in the state of the art to provide secondary enhancers with a better degree of regulation of signal amplification, compared to that obtained with the 4-aminopyridines of US Pat. Appl. 2008/0241686.

OBJECT AND SUMMARY OF THE INVENTION

Thus, object of the represent invention is to provide a new method for increasing and regulating light emission generated by the chemiluminescent reaction of luminol, a peroxydase, an oxidant and an electron mediator.

According to the invention, the above object is achieved thanks to the compositions specified in the ensuing claims, which are understood as forming an integral part of the present description.

In an embodiment, this invention provides for the use, in chemiluminescent compositions, of a secondary enhancer belonging to the class of N-azoles. The secondary enhancers of this invention include in particular the following N-azoles: imidazole, 1-methylimidazole, 1,2,3-triazole and 1,2,4-triazole.

A N-azole is defined as a class of five-membered nitrogen heteroaromatic ring compounds containing at least one other (non-carbon) atom of nitrogen.

Although the present invention concerns the use, in general and whatever purposes of azoles to increase and regulate light emission produced by the chemiluminescent reaction, it is however, primarily applicable in the context of an assay.

The term "assay" means the detection, semiquantification and quantification of an analyte. Typically, the implementation of an assay requires to relate the light output to the amount of peroxidase used, so that peroxidase is the substance determined directly. Although the present invention is useful for determining the presence or amount of any of the reaction partners (luminol; peroxidase; oxidant; mediator of electrons; N-azole as secondary enhancer), the reaction partner is not necessarily the substance itself to be determined. For example, the oxidant can be produced by a previous reaction, or a series of previous reactions.

Peroxidase or luminol may be present in the form of a conjugate with a ligand able to bind the analyte of interest, like for example an antibody used in an immuno-enzymatic assay to determine an antigen, or an antigen to determine an antibody. Or peroxidase may be conjugated to a nucleotide, an oligonucleotide or a nucleic acid in hybridization assays. Therefore, the present invention is applicable to any method of diagnostic assay of an analyte whose presence or amount is related to the presence or amount of a partner reaction selected from the group consisting of luminol, a peroxidase enzyme, an oxidant, a primary enhancer, an N-azole as secondary enhancer, that co-react in a chemiluminescent reaction, whose emission of light is detected or measured so that the presence or the amount of analyte to be analyzed is related to the production of light. The present invention also includes a kit for performing an assay comprising luminol, an oxidant, an electron mediator as primary enhancer and an azole as secondary enhancer. The kit may further comprise also a peroxidase enzyme, optionally labeled to or suitable to be labeled to a ligand specific for the analyte to be assayed.

BRIEF DESCRIPTION OF THE DRAWINGS

The invention will now be described, by way of example only, with reference to the enclosed figures of drawing, wherein.

DETAILED DESCRIPTION OF THE INVENTION

The secondary enhancers of this invention include in particular the following N-azoles: imidazole, 1-methylimidazole, 1,2,3-triazole and 1,2,4-triazole. These compounds are particularly useful in chemiluminescent assays that require a high and steady level of light output, such as blotting assays, including Western, Southern and Northern blots, as well as dot blot and nucleic acid hybridization assays.

Imidazole is well known to be a catalyst for peroxyoxalate chemiluminescence (T. Jonsson and K. Irgum, Anal. Chim. Acta 1999; 400:257-264; T. Jonsson and K. Irgum, Anal. Chem. 2000; 72:1373-1380). However, the above described systems are not comparable to those object of the current invention. Thus, are assigned to different classes, as illustrated in K. D. Gundermnann and F. McCapra, in "Chemiluminescence in Organic Chemistry", Springer 1987, namely Class IV—Peroxalate Chemiluminescence vs. Class V—Luminol and Related Compounds. In particular, it is known that certain organic oxalates react with hydrogen peroxide to produce unstable peroxyoxalates, which immediately decompose to $CO_2$. A fluorofore is added to the mixture, capable of undergoing chemical initiated electron exchange chemiluminescence. Acylation catalysts, such as imidazole or 4-dimethylaminopyridine are known to catalyze the formation of peroxalates, thus increasing light output. These reactions occur in polar aprotic solvent such as acetonitrile and are very fast, being over in a matter of seconds. They are clearly not especially suitable for the development of immunoenzymatic assays.

The concentration of N-azole enhancer is generally in the interval between 0.001 and 200 mmol/liter, preferably between 0.1 mmol and 50 mmol/liter. In particular, the concentration of imidazole is generally in the interval between 0.1 mmol and 50 mmol/liter.

Figure 1:
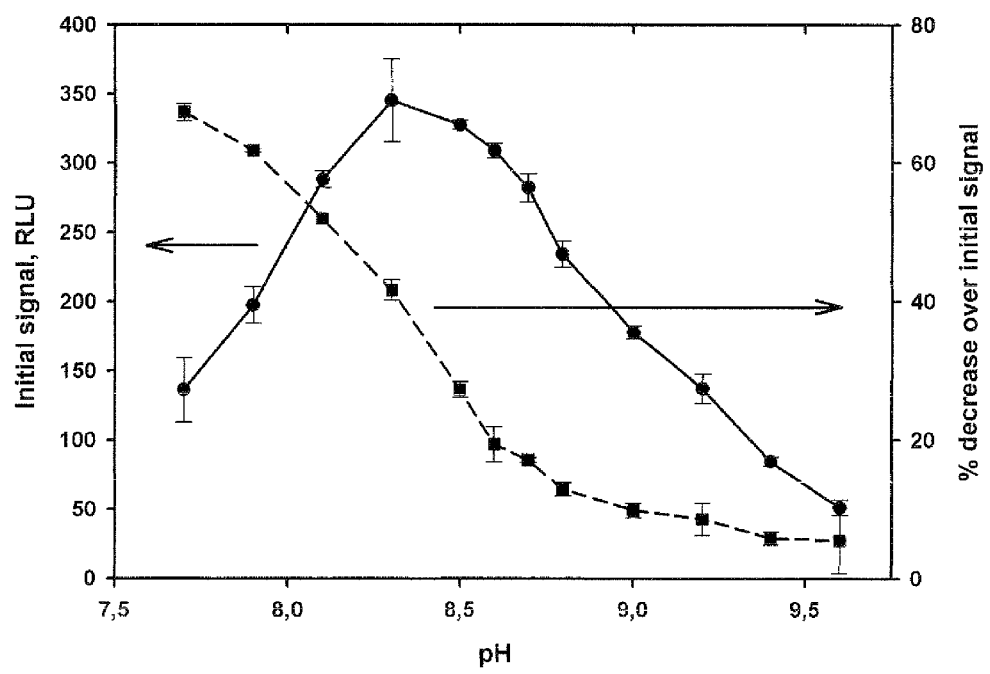
FIG. 1 shows a graph of the chemiluminescent signal (initial value and percent signal decay after a 900 second period) as a function of pH with imidazole as secondary enhancer.
Figure 2:
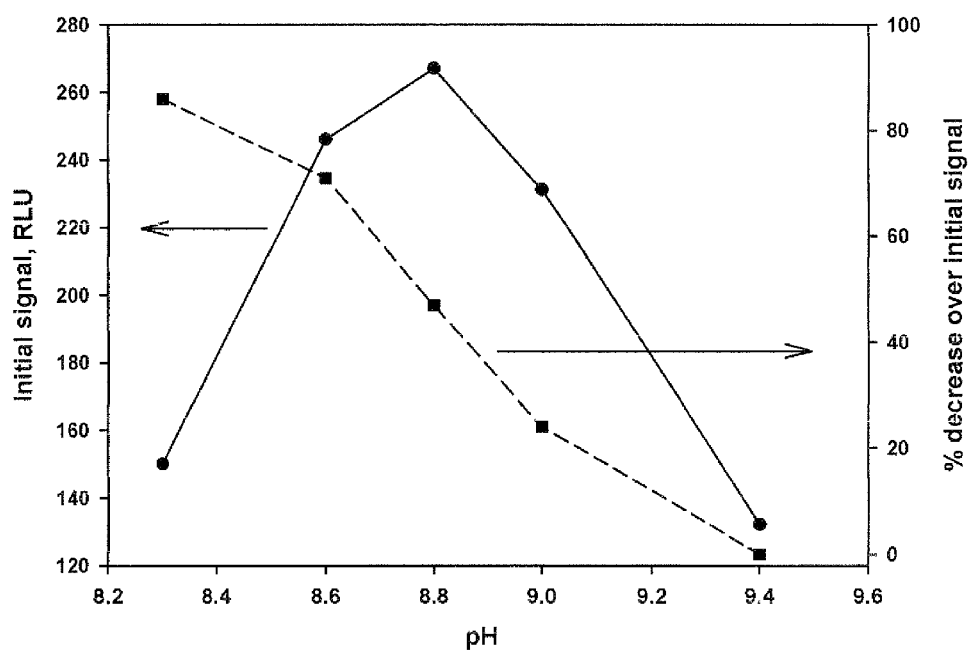
FIG. 2 shows a graph of the chemiluminescent signal (initial value and percent signal decay after a 900 second period) as a function of pH with 1-methylimidazole as secondary enhancer.
Figure 3:
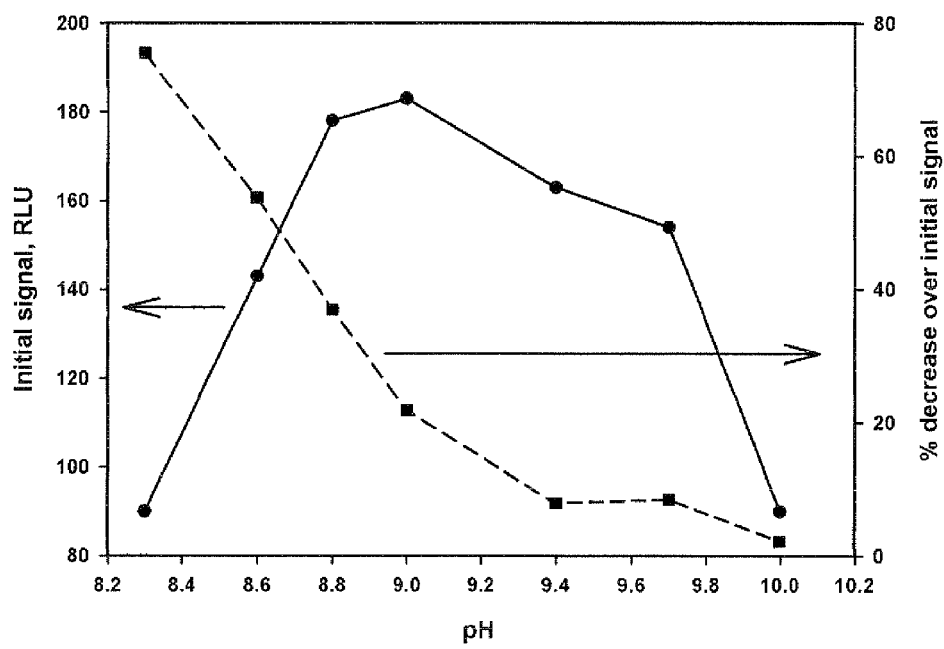
FIG. 3 shows a graph of the chemiluminescent signal (initial value and percent signal decay after a 900 second period) as a function of pH with 1,2,4-triazole as secondary enhancer.

In all cases, pH dependence of initial light output follows a bell-shaped curve. The best results in terms of initial light output are obtained generally at a pH lower than 9.1; in particular the best results are obtained in the pH range between 8.3 and 8.6 for imidazole and 1-methyl imidazole, FIGS. 1 and 2, while for 1,2,4-triazole the optimum shifts to higher pH interval, preferably between 8.6 and 9.3, FIG. 3.

On the other hand, light signal stability, calculated as the percent decrease of the initial light signal after 15 minutes, follows a sigmoid-shaped curve in all cases. The inflection point of the sigmoids occurs at approximately the same pH value as the maximum value of the initial signal.

Figure 4:
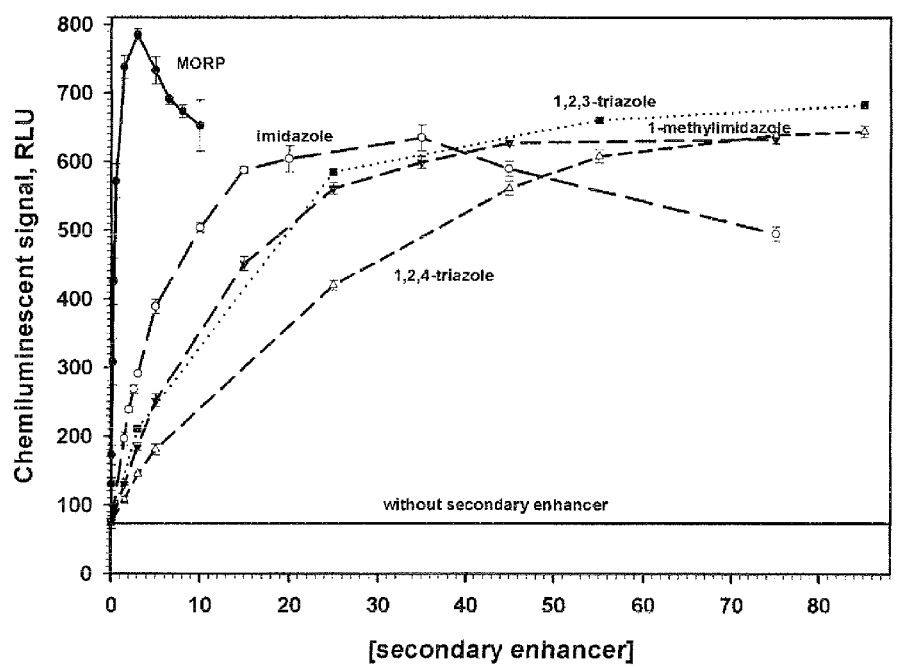
FIG. 4 shows as graph of the chemiluminescent signal as a function of the concentration of various secondary enhancers (MORP, imidazole, 1-methyl imidazole, 1,2,3-triazole, 1,2,4-triazole).

A graph showing the dependence of the initial light output upon secondary enhancer concentration is shown in FIG. 4. In contrast with the very sharp increase in light output observed even for very low concentrations of 4-morpholinopyridine (MORP), a typical 4-aminopyridine catalyst, the rise in signal intensity is much more gradual when N-azoles are employed as secondary enhancers. In addition, while MORP reaches a maximum effect at the concentration of 6 mM and then sharply decreases its enhancement effect with a further increase in concentration, N-azoles either begin to slowly decrease their action at very high concentration, e.g. imidazole, or else they tend to reach a plateau (1-methylimidazole, 1,2,4-triazole and 1,2,3-triazole).

It is clear from these data that the use of secondary enhancers based on N-azoles allows a much higher degree of control upon the chemiluminescent reaction compared to the previously known class of 4-aminopyridines. It is thus possible, through the use of N-azoles, to tightly regulate both initial light signal and its duration. This feature is very valuable, as it allows preparing chemiluminescent HRP substrates finely tuned to a specific use. For example, it may be useful to obtain a more moderate enhancement effect, together with a much longer signal duration, as to maximize the total amount of light produced in a given window of exposure. It is thus possible to optimize a chemiluminescent substrate according to the method of light detection, e.g. film vs. electronic devices, such as charged-coupled device (CCD), which have conflicting characteristics.

As for the reaction mechanism responsible for the observed effect of the N-azole secondary enhancers, it may be somewhat similar to that suggested for the 4-aminopyridines, e.g. nucleophilic attack upon the diazaquinone, L, with production of an intermediate more reactive toward hydrogen peroxide. The differences between N-azoles and 4-aminopyridines may be ascribable to their different nucleophilicities.

As for the other components of the enzymatic substrates of this invention, the following specifications are applicable.

The luminol used must be of a purity suitable and appropriate for luminescence assays. Luminol can be used as the sodium salt. The concentration of luminol in the chemiluminescent substrate is generally between 0.1 mmol/liter and 50 mmol/liter, preferably between 0.5 and 10 mmol/liter.

The oxidant can be any substance capable of oxidizing luminol with the production of light. A source of peroxide is preferred, such as hydrogen peroxide or sodium perborate. The concentration of oxidant used in the chemiluminescent substrate is between 0.1 and 100 mmol/liter, preferably between 0.5 and 10 mmol/liter.

The primary enhancer (electron mediator) can be any electroactive substance able to act as electron mediator between the oxidant and the luminol. In particular, enhancers belonging to the following classes of compounds: benzothiazoles, phenols, aromatic amines, N-alkyl phenothiazines, indophenols, arylboronic acids. The preferred enhancers are: p-iodophenol, p-iodophenylboronic acid, salts of 3-(phenothiazine-10-yl)propane-1-sulfonic or 4-(phenothiazine-10-yl)butane-1-sulfonic acid. The primary enhancer must be of adequate and appropriate purity for use in chemiluminescence assays. In particular, it must not contain impurities that can inhibit the chemiluminescent reaction. The concentration of primary enhancer used in the chemiluminescent assays of peroxidase according to this invention is comprised between 0.001 and 20 mmol/liter, preferably between 0.1 and 10 mmol/liter.

The peroxidase enzyme is any peroxidase suitable for use in luminescence assays. In particular, it can be horseradish peroxidase, for example Sigma type VI A or IX. It can also be an anionic peroxidase, for example soybean peroxidase or sweet potato peroxidase. The peroxidase can be free or conjugated to ligand, or a biopolymer, or a solid phase.

The chemiluminescent reactions of this invention are applicable to the detection and quantification of analytes, using, for example, the formation of a bond between a protein or nucleic acid and a membrane and peroxidase as tracer. The luminescent reaction is initiated by adding the chemiluminescent substrate to the membrane. The emission of light is prolonged and can be measured by film, camera or other instrumentation.

The chemiluminescent substrate, comprised of luminol, a source of peroxide (the oxidant), a primary enhancer and a N-azole as secondary enhancer can be conveniently prepared in a kit form, as known in the art. In particular, the luminol and the peroxide are best formulated as separate solutions (vials), e.g., A and B, as to prolong their shelf life. Primary and secondary enhancers, as well as other additives, such as chelators and stabilizers can be added to either luminol or peroxide solutions/vials, or both. The two kit solutions also contain buffering substances, and are formulated in such a manner that upon mixing, the chemiluminescent substrate, or "working solution", reaches an optimum pH value. The peroxidase enzyme is not stored together with its substrate component, but as a separate ingredient, normally as a conjugate with the ligand for the substance/analyte of interest, and can be also realized by the final user.

The chemiluminescent assays based on the substrate solution of this invention include dot blot and western blot assays for proteins and Southern and Northern Blots assays for nucleic acids. The blot assays uses gel electrophoresis to separate the analyte of interest (a protein or a nucleic acid molecule) from the other components (other proteins or other nucleic acid molecules) present in the sample to be tested. The analyte and the other components are then transferred to a membrane, where they are probed (detected) using ligand (antibodies, oligonucleotide probes) specific to the analyte.

Another important application of the chemiluminescent substrates of this invention is in ELISA immunoenzymatic assays, especially for analytes present in extremely small quantities, such as tumor markers, thyroid hormones, protein viruses (HIV, HCV, HPV), or steroid hormones (estradiol, aldosterone). Performing an ELISA assay for detecting an analyte, the assay involves at least one ligand (detection agent) with specificity for the analyte of interest. The analyte within the sample is immobilized on a solid support (usually a polystyrene microtiter plate) either non-specifically (via adsorption to the surface) or specifically (via capture by another ligand specific to the same analyte, in a "sandwich" ELISA). After the analyte is immobilized, the detection agent is added, forming a complex with the analyte. The detection agent can be covalently linked to a peroxidase enzyme, or can itself be detected by a secondary detecting agent that is linked to a peroxidase enzyme through bioconjugation (like for example via biotin or streptavidin). Between each step, the plate is typically washed with a mild detergent solution to remove any proteins or antibodies that are not specifically bound. After the final wash step, the plate is developed by adding the enzymatic substrate (the chemiluminescent substrate herein described) to produce a light signal, which indicates the quantity of analyte in the sample.

EXAMPLES

The following examples serve to illustrate specific aspects of the invention. However, they are not intended to limit the invention.

Naturally, while the principle of the invention remains the same, the details of construction and the embodiments may vary widely with respect to what has been described and illustrated by way of example, without departing from the scope of the present invention.

All the reagents used within the present application were purchased from Sigma-Aldrich.

All measurements reported in Examples were carried out with a Varian Eclipse spectrofluorimeter and the following settings: bio/chemiluminescence mode; emission wavelength: 425 nm; emission slit: 20 nm; Photomultiplier Detection Voltage: medium.

Example 1 pH dependence of imidazole on the luminol-peroxide-sodium 3-(phenothiazin-10-yl)propane-1-sulfonate-peroxidase reaction A chemiluminescent substrate was prepared with the following composition:
[luminol sodium salt]=5 mM
[sodium perborate]=4 mM
[sodium 3-(phenothiazin-10-yl)propane-1-sulfonate]=3 mM
[imidazole]=10 mM
In 0.15 mM Tris Buffer, pH 9.0

A series of disposable polymethylmethacrylate cuvettes is prepared, each containing 2 mL of substrate solution. To each cuvette are added small amounts of 5 M HCl or 5 M NaOH, in order to adjust the pH in the 8.0-10.0 range without producing in any case significant changes in the total volume. To each cuvette are added 10 μL of a 2 μg/mL horseradish peroxidase solution (HRP-type VIA) and simultaneously a 30 seconds countdown is started. The cuvette is closed with a square piece of parafilm and vortexed for 3 seconds. The cuvette is then inserted into the spectrofluorimeter. At the end of the 30 seconds countdown measurement of the luminescent signal is initiated and recorded for a 900 sec period. In all cases the signal reaches a plateau level within 30 seconds after the addition of the peroxidase, and then begins to slowly decrease. Initial signal levels, as well as % signal decrease during the first 900 min are plotted vs. pH, FIG. 1.

Example 2 pH dependence of 1-methylimidazole on the luminol-peroxide-sodium 3-(phenothiazin-10-yl)propane-1-sulfonate-peroxidase reaction A chemiluminescent substrate was prepared with the following composition:
[luminol sodium salt]=5 mM
[sodium perborate]=4 mM
[sodium 3-(phenothiazin-10-yl)propane-1-sulfonate]=3 mM
[1-methylimidazole]=10 mM
In 0.15 mM Tris Buffer, pH 9.0
The same experimental procedure is used as described in Example 2. Initial signal levels, as well as % signal decrease during the first 900 min are plotted vs. pH, FIG. 2.

Example 3 pH dependence of 1,2,4-triazole on the luminol-peroxide-sodium 3-(phenothiazin-10-yl)propane-1-sulfonate-peroxidase reaction A chemiluminescent substrate was prepared with the following composition:
[luminol sodium salt]=5 mM
[sodium perborate]=4 mM
[sodium 3-(phenothiazin-10-yl)propane-1-sulfonate]=3 mM
[1,2,4-triazole]=10 mM
In 0.15 mM Tris Buffer, pH 9.0
The same experimental procedure is used as described in example 2. Initial signals, as well as % signal decrease during the first 900 min are plotted vs. pH, FIG. 3.

Example 4

Dependence of the sodium 3-(phenothiazin-10-yl)propane-1-sulfonate enhanced luminol-peroxide-peroxidase reaction on secondary enhancer concentration A series of chemiluminescent substrates in 0.15 M, pH 9.00+−0.05 Tris buffer, is prepared, with the following compositions:
[luminol sodium salt]=5 mM
[sodium perborate]=4 mM
[sodium 3-(phenothiazin-10-yl)propane-1-sulfonate]=3 mM
secondary enhancer=MORP, imidazole, 1-methylimidazole, 1,2,3-triazole, 1,2,4-triazole at the following concentrations:
[MORP]=0.025 mM, 0.05 mM, 0.125 mM, 0.25 mM, 0.5 mM, 1.5 mM, 3 mM, 5 mM, 6.5 mM, 8 mM, 10 mM.
[imidazole]=1.5 mM, 2 mM, 2.5 mM, 3 mM, 5 mM, 10 mM, 15 mM, 20 mM, 35 mM, 45 mM, 75 mM.
[1-methylimidazole]=1.5 mM, 3 mM, 5 mM, 15 mM, 25 mM, 35 mM, 45 mM, 75 mM.
[1,2,3-triazole]=3 mM, 25 mM, 55 mM, 85 mM.
[1,2,4-triazole]=1.5 mM, 3 mM, 5 mM, 25 mM, 45 mM, 55 mM, 75 mM, 85 mM.

A series of disposable polymethylmethacrylate cuvettes is prepared, each containing 2 mL of substrate solution. To each cuvette are added 10 μL of a 2 μg/mL horseradish peroxidase solution (HRP-type VIA) solution and simultaneously a 30 seconds countdown is started. The cuvette is closed with a square piece of parafilm and vortexed for 3 seconds. The cuvette is then inserted into the spectrofluorimeter. At the end of the 30 seconds countdown measurement of the luminescent signal is initiated and recorded for a 900 sec period. In all cases the signal reaches a plateau level within 30 seconds after the addition of the peroxidase, and then begins to slowly decrease. Initial, plateau levels are plotted vs. secondary enhancer concentration, FIG. 4. As it can be seen, the effect of MORP on signal intensity is quite strong even at very low concentrations. Signal output reaches a sharp maximum at about 1.5 mM of MORP and then falls abruptly. In contrast, N-azoles exert a much more gradual effect on signal intensity, reaching a plateau at much higher concentration levels. Thus, they afford a considerable degree of regulation of the chemiluminescent light output, which cannot be obtained with dialkylaminopyridine secondary enhancers such as MORP.

Example 5

Substrates for Measuring Peroxidase by Chemiluminescence

To ensure long term stability, the components of the chemiluminescent substrate can be provided as separate solutions, which, when needed, can be mixed to produce a Working Solution. For examples, a Working Solution for the measurement of peroxidase can be obtained by mixing equal parts of the following solutions:
Substrate (1):
Solution A:
[luminol sodium salt]=2 mM
[sodium 3-(phenothiazin-10-yl)propane-1-sulfonate]=0.3 mM
[imidazole]=0.25 mM
In 0.10 mM Tris Buffer, pH 9.6
Solution B:
[sodium perborate]=8 mM
In 50 mM, pH 5.0 acetate buffer
The pH of the Working Solution, after mixing Solution A and B, is 9.0.
Substrate (2):
Solution A:
[luminol sodium salt]=10 mM
[sodium 3-(phenothiazin-10-yl)propane-1-sulfonate]=1.5 mM
[imidazole]=1.0 mM
In 0.25 mM Tris Buffer, pH 9.6
Solution B:
[sodium perborate]=8 mM
In 50 mM, pH 5.0 acetate buffer
The pH of the Working Solution, after mixing Solution A and B, is 9.0.
Substrate (3):
Solution A:
[luminol sodium salt]=10 mM
[sodium 3-(phenothiazin-10-yl)propane-1-sulfonate]=6 mM
[imidazole]=40 mM
In 0.30 mM Tris Buffer, pH 9.3
Solution B:
[sodium perborate]=8 mM
In 50 mM, pH 5.0 acetate buffer The pH of the Working Solution, after mixing Solution A and B, is 8.6.

Example 6

Total Akt Western Blot Assay

The blotting method used is described by H. Towbin at al Proc. Acad. Sci. 76, 4350-4353 (1979). Serial dilutions of C2C12 cell lysates were separated by gel electrophoresis on 12% sodium dodecylsulfate (SDS) polyacrylamide gel. The gel was transferred to a nitrocellulose membrane for Western Blot. Non-specific binding sites were blocked with a 5% milk powder solution for 1 hour and then washed several times with a wash buffer (20 mM Tris, 137 mM NaCl). The blots were then incubated with rabbit anti-total Akt at 1:20,000 dilution for one hour, then washed as above to remove the antibody not linked to the antigen. The membrane with the blot was incubated for 1 hour with the secondary antibody labeled with HRP (goat anti-rabbit, dilution 1:100,000). A Working Solution was prepared, according to Example 5, Substrate (2). The Working Solution was then added to the membrane and incubated for five minutes. The chemiluminescent signal was acquired using autoradiographic film with a 1 minute exposure. Autoradiographic images were scanned and digitized. Results were comparable to those obtained using a commercial chemiluminescent substrate (SuperSignal Dura, ThermoScientific).

Example 7

Human Thyroglobulin ELISA Assay

This immunometric assay is based on the immunochemical reaction between a capture antibody, an antigen (Human Thyroglobulin, Tg), and soybean peroxidase (SbP)-labeled antibody. Wells with capture antibody were prepared by incubating the microwell plates coated with streptavidine with a solution of biotinylated capture antibody. The wells were then incubated with Tg calibrators from a commercial kit. After an incubation period of one hour at 37° C., the plate was washed with PBS-0.05% Tween-20. 200 μL of solution of a peroxidase-labeled anti-Tg antibody were then added to each well. The wells were incubated at room temperature for 1 hour and then washed to remove excess conjugate. A chemiluminescent Working Solution prepared as described in Example 5, Substrate 3, was added to the wells and incubated for ten minutes. A lower detection limit (LOD) for Tg of 0.2 ng/mL was obtained. This value was identical to the LOD obtained with a commercial kit based on the alkaline phosphatase/dioxetane detection system.

The invention claimed is:

1. A method for increasing the light emission produced by the chemiluminescent reaction of luminol, a peroxidase enzyme, an oxidant and a primary enhancer, wherein said primary enhancer is sodium 3-(phenothiazin-10-yl)propane-1-sulfonate, and wherein said chemiluminescent reaction occurs in the presence of a secondary enhancer wherein said secondary enhancer is selected from the group consisting of imidazole, 1-methylimidazole, 1,2,3-triazole, and 1,2,4-triazole.

2. The method according to claim 1, wherein said peroxidase enzyme is selected from the group consisting of horseradish peroxidase, soybean peroxidase, and sweet potato peroxidase.

3. The method according to claim 1, wherein said peroxidase is free or conjugated to a ligand.

4. The method according to claim 1, wherein said oxidant is sodium perborate or hydrogen peroxide.

5. The method according to claim 1, wherein said chemiluminescent reaction is carried out at a off between 8.0 and 10.0.

6. The method according to claim 1, wherein said chemiluminescent reaction is carried out at a pH between 8.3 to 9.3.

7. A method for performing a blot assay of an analyte in a sample, wherein said method employs a method for increasing the light emission produced by the chemiluminescent reaction of luminol according to claim 1 as means of detection and quantification of said analyte.

8. A method for performing an ELISA assay of an analyte in a sample, wherein said method employs a method for increasing the light emission produced by the chemiluminescent reaction of luminol according to claim 1 as means of detection and quantification of said analyte.

9. A kit for performing an assay for determining an analyte in a sample, wherein the kit comprises luminol, an oxidant, a primary enhancer in a form of an electron mediator, wherein said primary enhancer is sodium 3-(phenothiazin-10-yl)propane-1-sulfonate, and a secondary enhancer is selected from the group consisting of imidazole, 1-methylimidazole, 1,2,3-triazole, and 1,2,4-triazole.

10. The kit according to claim 9, wherein luminol is present in a first vial and the oxidant is present in a second vial, and wherein the primary enhancer and the secondary enhancer are present either in the first vial or in the second vial or in both vials.

11. The kit according to claim 9, wherein the kit further comprises a peroxidase enzyme.

12. The kit according to claim 9, wherein luminol or the peroxidase enzyme are conjugated or are suitable to be conjugated to a ligand able to bind the analyte.

13. The kit according to claim 11, wherein said peroxidase enzyme is selected from the group consisting of horseradish peroxidase, soybean peroxidase, and sweet potato peroxidase.

14. The kit according to claim 9, wherein said oxidant is sodium perborate or hydrogen peroxide.

* * * * *